US007147663B1

(12) United States Patent
Berg et al.

(10) Patent No.: US 7,147,663 B1
(45) Date of Patent: Dec. 12, 2006

(54) ARTIFICIAL HEART VALVE ATTACHMENT APPARATUS AND METHODS

(75) Inventors: Todd Allen Berg, Lino Lakes, MN (US); William J. Swanson, St. Paul, MN (US); Jerry Grudem, St. Louis, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 694 days.

(21) Appl. No.: 09/550,471

(22) Filed: Apr. 14, 2000

Related U.S. Application Data

(60) Provisional application No. 60/130,758, filed on Apr. 23, 1999.

(51) Int. Cl.
*A61F 2/24* (2006.01)

(52) U.S. Cl. .................. 623/2.38; 623/1.26; 623/2.1

(58) Field of Classification Search .......... 623/2.38, 623/900, 2.4, 2.41, 2.39, 1.26, 2.18, 2.19, 623/2.1
See application file for complete search history.

(56) References Cited

U.S. PATENT DOCUMENTS

| 3,143,742 A | | 8/1964 | Cromie | |
| 3,464,065 A | * | 9/1969 | Cromie | 623/2 |
| 3,526,906 A | | 9/1970 | Laszlo | |
| 3,546,710 A | * | 12/1970 | Shumakov et al. | 623/2 |
| 3,574,865 A | * | 4/1971 | Hamaker | 623/2 |
| 3,686,740 A | | 8/1972 | Shiley | 29/439 |
| 5,824,064 A | | 10/1998 | Taheri | 623/2 |
| 5,843,164 A | * | 12/1998 | Frantzen et al. | 623/1 |
| 5,843,170 A | | 12/1998 | Ahn | 623/1 |
| 5,855,601 A | * | 1/1999 | Bessler | 623/2 |
| 5,976,178 A | | 11/1999 | Goldsteen | 623/1 |
| 6,106,550 A | * | 8/2000 | Magovern et al. | 623/2.38 |
| 6,197,054 B1 | * | 3/2001 | Hamblin et al. | 623/2.38 |
| 6,241,765 B1 | * | 6/2001 | Griffin et al. | 623/2.38 |
| 6,416,535 B1 | * | 7/2002 | Lazarus | 623/1.11 |

FOREIGN PATENT DOCUMENTS

| DE | 196 05 042 A | 1/1998 |
| WO | WO 97/10757 | 3/1997 |
| WO | WO 99/04724 | 2/1999 |
| WO | WO 99/18887 | 4/1999 |
| WO | WO 99/56665 | 11/1999 |

* cited by examiner

*Primary Examiner*—Bruce E. Snow
(74) *Attorney, Agent, or Firm*—Fish & Neave IP Group of Ropes & Gray LLP; Joel Weiss; Hong Lin

(57) ABSTRACT

Heart valve attachment apparatus and methods that significantly reduce attachment times are provided. The apparatus and methods utilize a connector band to form an interface between a uni-directional valve and a tissue annulus. The connector band is secured to the tissue annulus by retention fingers.

11 Claims, 13 Drawing Sheets

ARTIFICIAL HEART VALVE ATTACHMENT APPARATUS AND METHODS

CROSS-REFERENCE TO RELATED APPLICATION

This application claims priority from U.S. Provisional Patent Application No. 60/130,758, filed Apr. 23, 1999.

BACKGROUND OF THE INVENTION

This invention relates to apparatus and methods for attaching replacement heart valves.

The replacement of a defective heart valve requires an open heart procedure in which the old, defective, valve is removed and replaced with an artificial valve. Generally, this procedure requires the heart to be placed on a cardiopulmonary bypass (CPB) to allow the heart to be stopped and the new valve to be carefully sewn in place.

This method of valve attachment, commonly known as suturing, is an effective method of attaching the new heart valve to the heart. However, it requires significant time and skill to complete. Therefore, extended CPB time is required. The extended CPB time associated with suturing, in conjunction with the complex nature of the procedure itself, may increase the likelihood of complications, including stroke, heart block and long patient recovery times.

Therefore, it would be desirable to provide heart valve attachment apparatus and methods that significantly reduce attachment times.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout.

SUMMARY OF THE INVENTION

It is an object of the invention to provide heart valve attachment apparatus and methods that significantly reduce attachment times.

A valve apparatus for deploying in, and securing to, a tissue annulus, includes: a uni-directional valve portion for passing fluid in one direction and obstructing fluid in an opposite direction, a connector band located circumferentially around, and attached to, the valve portion and a plurality of fingers located circumferentially around, and attached to, the band. The fingers are adapted to secure the valve to the tissue annulus.

In an alternative embodiment, a connector band can be deployed separate from the valve portion. After the band is deployed, a valve can be attached to the band by screws, pop rivets or other suitable attachment device or method.

In another alternative embodiment, fingers can be implemented on the valve portion itself, thereby obviating the need for a connector band.

DETAILED DESCRIPTION OF THE INVENTION

This invention relates to heart valves which are modified so that the valve can be attached to the heart without the need for suturing. Significant technology has been developed related to replacing sutures in bypass grafting—i.e., attaching a tissue conduit to another with a mechanical connector rather than sewing the conduits to each other to form the anastamosis. Examples of such technology are found in commonly assigned U.S. Pat. No. 5,976,178 and co-pending commonly assigned patent application Ser. Nos. 08/839,199, 08/946,742, 09/016,721, 09/187,335, 09/187,361 and 09/186,774, all of which are incorporated by reference herein in their entireties.

These references, at least in part, disclose inventions related to methods and apparatus for attaching synthetic or biological tissue grafts without the need for sutures. Portions of the references deal specifically with methods and apparatus for attaching synthetic or biological tissue grafts to a connector, which is then secured to a blood vessel—e.g., the aorta—by using hooked or barbed fingers. In certain embodiments, the fingers are formed from an elastic material—e.g., nitinol wire. In these embodiments, the fingers may be stretched or otherwise manipulated to pierce the tissue graft and retain the tissue graft with the hooked or barbed ends of the fingers. The elasticity of the fingers then causes the fingers to snap back such that the tissue graft is secured to the connector. The connector is then connected to a blood vessel to complete an anastamosis.

Alternatively, the fingers may be formed from relatively non-elastic stainless steel. In these embodiments, the fingers are deformed to properly engage the tissue graft and then mechanically crimped to seal the connector to the tissue graft.

The present invention provides methods and apparatus for using retention fingers, such as the fingers described above, to attach heart valves to hearts.

Figure 1:
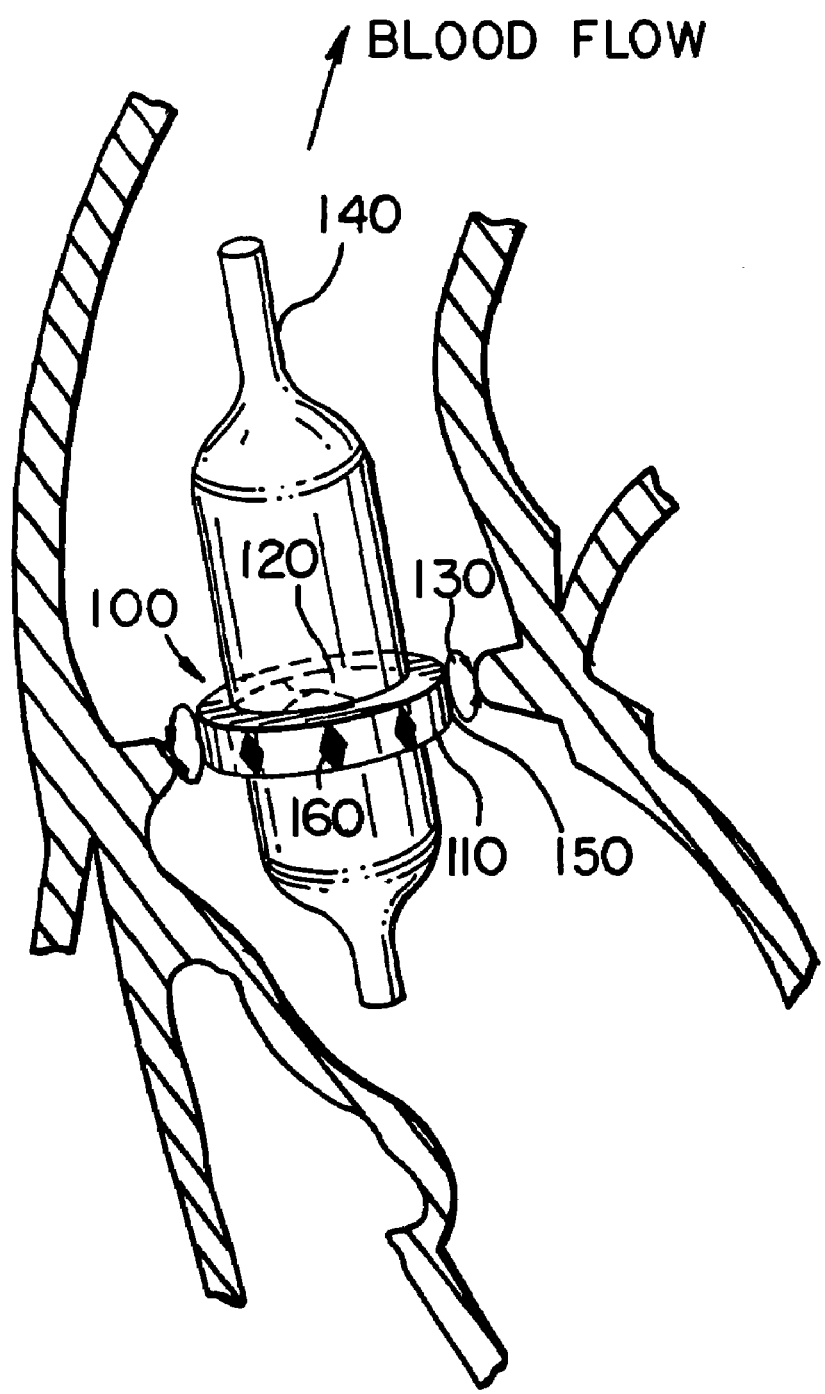
FIG. 1 is an elevational view of a preferred embodiment of a heart valve according to the invention.

FIG. 1 shows an artificial heart valve 100 having a balloon expandable connector band 110 with a one-way valve portion 120 integrated within connector band 110. Valve 100 is positioned for deployment in the left ventricle outflow valve of a heart (this location illustrates only one possible exemplary embodiment of the invention, and is not intended to limit the invention to use only in the left ventricle outflow valve.) Connector band 110 preferably includes a series of retention fingers 130 with barbed ends—i.e., the ends of the fingers have small projections that secure the fingers to their surface of engagement—or, alternatively, hooked ends—i.e., the ends of the fingers are bent—, or a combination of the two, spaced substantially circumferentially around band 110. Each finger preferably is attached adjacent to one end of the length of band 110 and has a corresponding finger that opposes it and is attached to the other end of the length of band 110. Thus, when the length of band 110 is reduced, the ends of each set of corresponding fingers 130 converge and engage the surrounding tissue.

The invention operates as follows: first, valve 100 is positioned for securing to the tissue annulus that surrounded the old valve. Then, balloon 140 is preferably positioned through the orifice of valve 100. Balloon 140 is then expanded. The positioning and expansion of balloon 140 can be accomplished by methods that are known to those in the art and explained in more detail in the references which are incorporated by reference above—e.g., U.S. Pat. No. 5,976,178.

Expansion of balloon 140 increases the circumference of band 110 to conform to, and substantially fill, the tissue annulus. As connector band 110 expands circumferentially, it shortens in length—i.e., the dimension of band 110 that is substantially parallel to the blood flow. The shortening in length causes the barbed heads on each corresponding pair of retention fingers 130 to converge and engage the surrounding tissue annulus, thereby securing valve 100 to the tissue annulus. When the heads of fingers 130 engage the tissue annulus, they preferably remain there permanently. Valve 120, which may preferably be formed from porcine tissue, or other suitable natural or synthetic tissue, can be pushed out of the way during expansion and then naturally returns following expansion.

Figure 2:
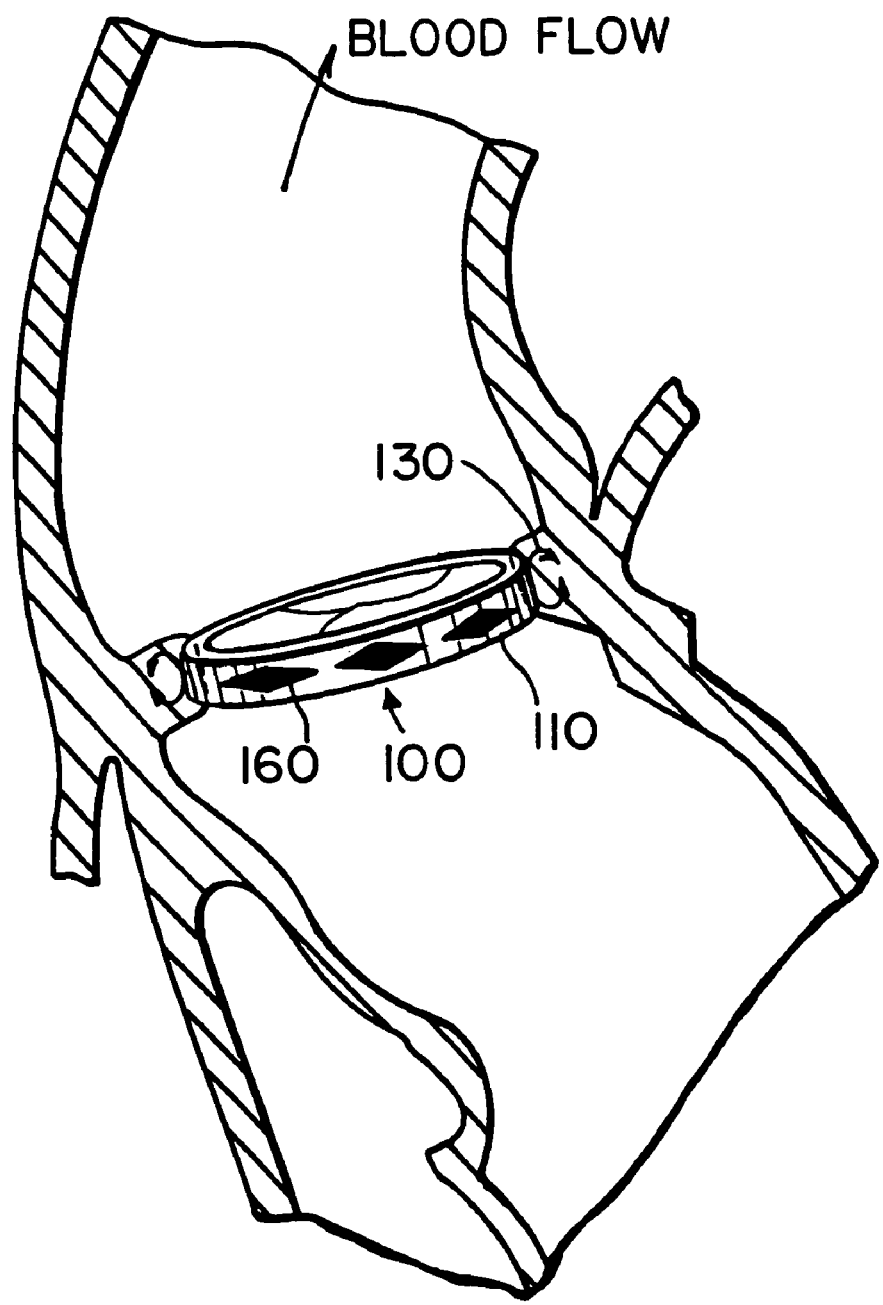
FIG. 2 is an elevational view of the heart valve of FIG. 1 in a deployed position.

FIG. 2 shows valve 100 after it has been deployed. Band 110 may be formed from expandable metal—i.e., metal that has been perforated and cut in such a way that it can be expanded in one or more directions by deforming the metal in the vicinity of the cuts and perforations. This type of structure is frequently found in stents used to prevent collapses of tubular body structures; and band 110 could be a converted stent, possibly with some modifications. Alternatively, band 110 may be constructed from an expandable open mesh framework (see mesh 360 in FIGS. 3 and 4)—e.g., a braid of nitinol, stainless steel, tungsten wires or polymer strands—which may be covered with a rubber-like web—e.g., of silicone—.

It should be noted that, following expansion of band 110, the diameter of band 110 has increased, while the length of band 110 has decreased. As the length of band 110 is decreased, the barbed heads of axially opposite fingers 130 converge, engage the tissue annulus, and secure valve 100 to the tissue annulus. The broadening and shortening of the black diamonds 160 shown in FIGS. 1 and 2 indicate the circumferential expansion and the lengthwise contraction of the metal. Following deployment, fingers 130 grab the tissue annulus and exert a force joining band 110 to the tissue annulus. The force exerted by the fingers on the tissue annulus forms a substantially leak-proof compression seal between band 110 and the tissue annulus. Thus, the tissue preferably forms a lip which abuts the valve portion 120 of valve 110.

The outer walls of band 110 may include a gasket-like material. In an alternative embodiment, a separate gasket 150 (shown in FIG. 1) may be attached around band 110. To further enhance the seal between band 110 and valve portion 120 the gasket-like material, or gasket 150, preferably conforms to the existing tissue annulus and seals the new valve to the tissue annulus to protect against leakage around, or through, band 110. Gasket 150 may preferably be formed from a soft, deformable biocompatible material—e.g., polyurethane, silicone, dacron or other suitable material—that readily conforms to existing tissue, yet provides a fluid-tight seal around valve 110.

Figure 3:
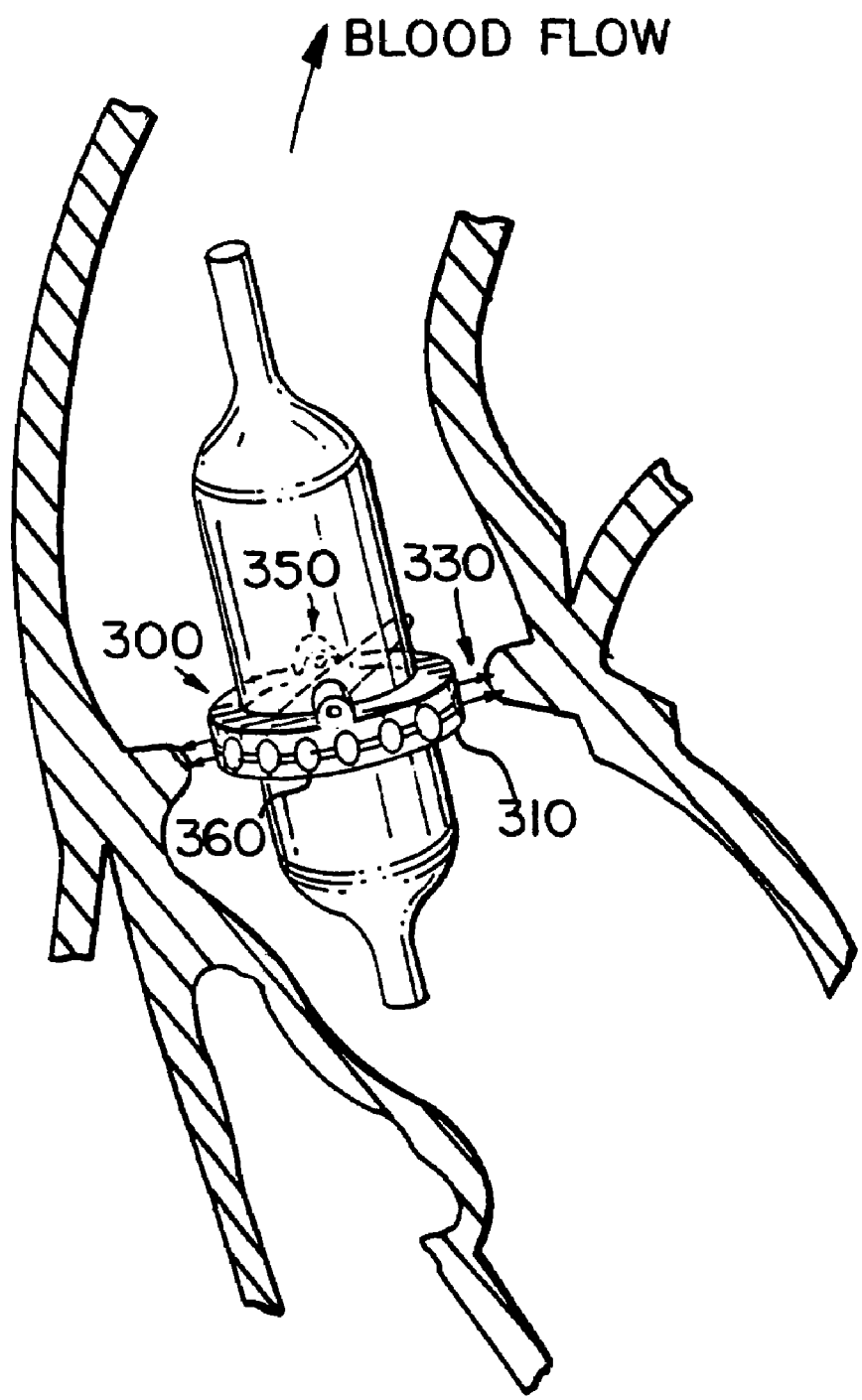
FIG. 3 is an elevational view of another embodiment of a heart valve according to the invention.

FIG. 3 shows another embodiment of an artificial heart valve 300 according to the principles of the invention. Valve 300 includes fingers 330 that are substantially perpendicular to the length of band 310.

Figure 4:
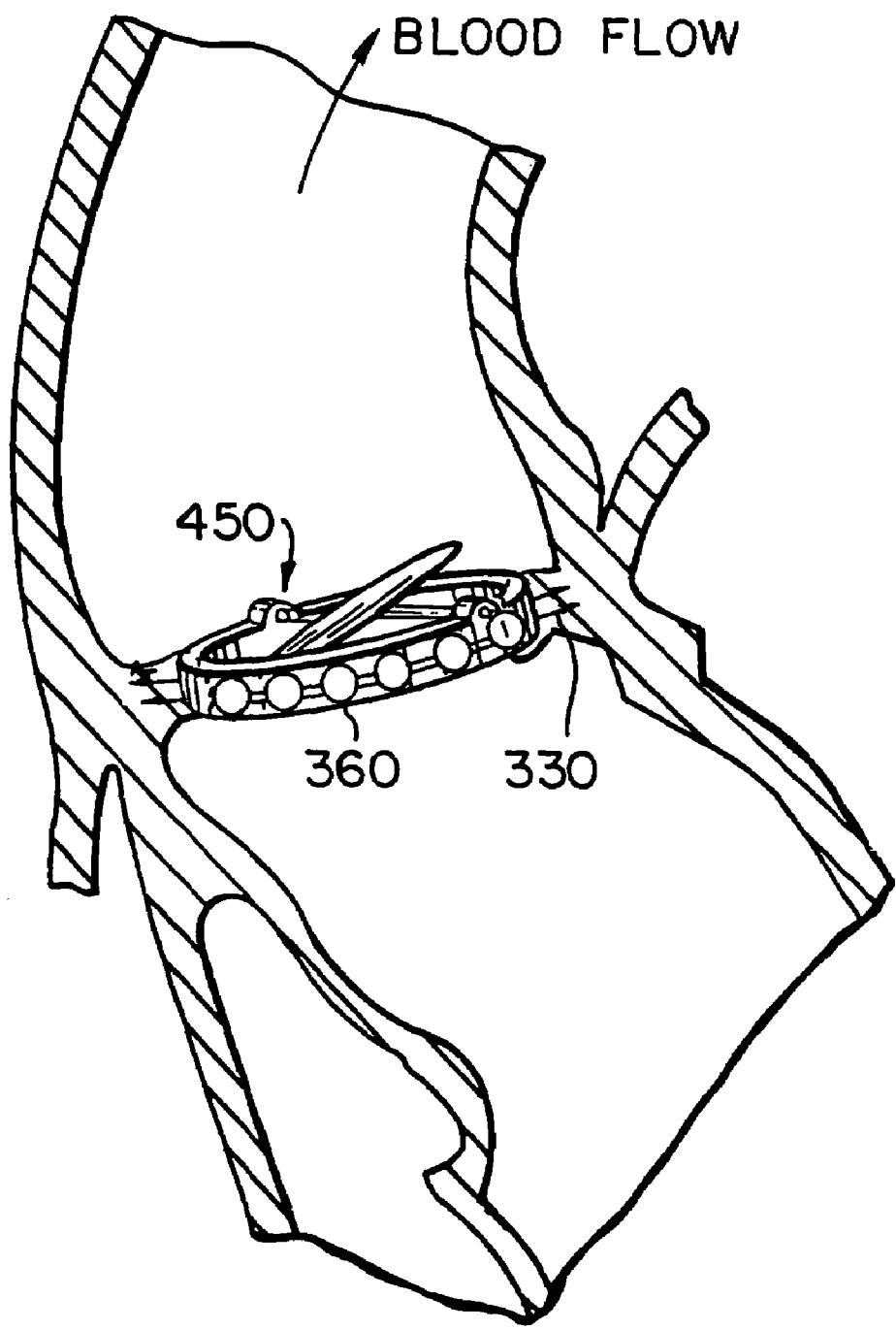
FIG. 4 is an elevational view of the heart valve of FIG. 3 in a deployed position.

FIG. 4 shows valve 300 after it has been deployed. Fingers 330 are shown secured to the tissue annulus by the barbed heads of fingers 330 and a compression seal is preferably formed between band 310 and the tissue annulus.

Figure 5:
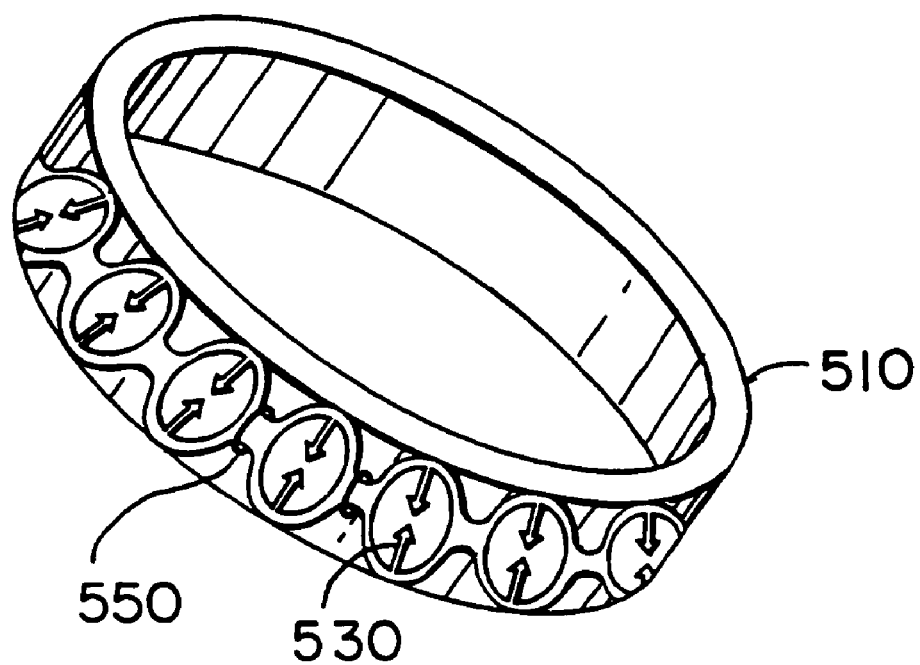
FIG. 5 is an elevational view of a connector band according to the invention.

FIG. 5 shows one embodiment of an band 510 suitable for deployment to attach to the tissue annulus as shown in FIGS. 3 and 4. At this stage, fingers 530 are parallel to the length of band 510. However, fingers 530 may be redirected radially outward, perpendicular to the length of band 510 by some suitable means. After redirection, fingers 530 may preferably appear similar to fingers 330 shown in FIGS. 3 and 4. Thereafter, band 510 can be further expanded such that fingers 530 engage, and are secured to, the tissue annulus.

One advantage of the embodiment shown in FIG. 5 is that the band can be positioned using suture threads or other suitable devices which can be attached to rings 550. Rings 550 may be linked to the infrastructure of fingers 530.

Band 510 should preferably be expandable. Fingers 530 can be oriented outward before expansion—e.g., during production of band 510. Then, band 530 is positioned within the tissue annulus. Thereafter, fingers 530 are secured to the tissue annulus upon expansion of band 510.

In an alternative embodiment of the invention, a connector band can also be deployed separate from a valve. In this embodiment, a band, such as band 510, may first be expanded and secured to the tissue annulus at the required implant site. Then, the valve can be incorporated into the band. To facilitate the connection of the band to the valve, the band may contain a number of holes or recesses adapted to receive screws from an implanted valve, or seats for rivets or clips which are used to secure the valve to the previously deployed band. Alternatively, rivets which require no-preformed seats, but are popped through a flat portion of the band may also be used to secure the valve to the band. Examples of recesses 350, 450 are shown in FIGS. 3 and 4. The recesses may preferably be located on the interior side of the band.

Figure 6:
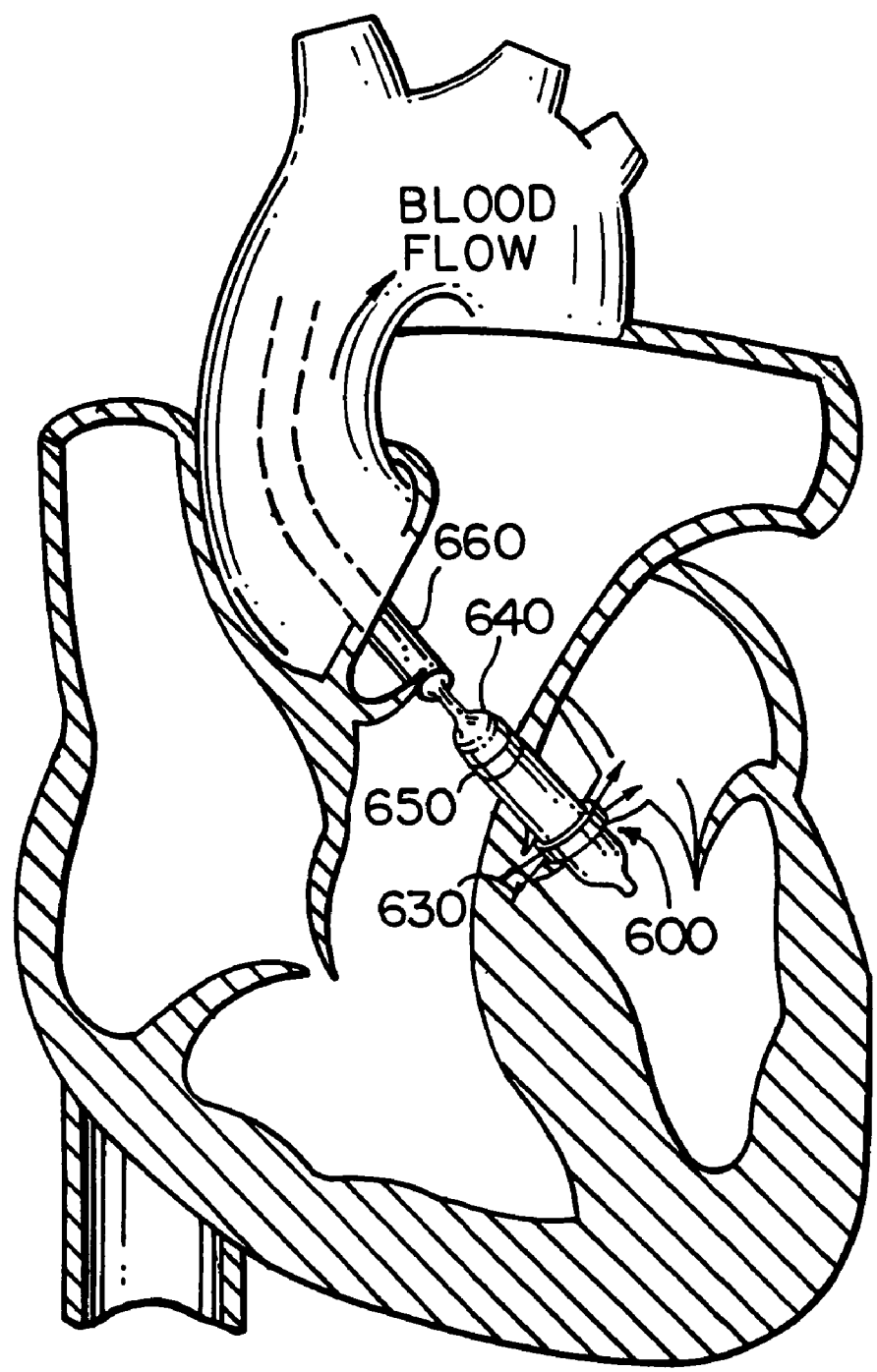
FIG. 6 is an elevational view of the heart valve of FIGS. 3 and 4 in a deployed position.

FIG. 6 shows an exemplary valve 600 deployed in a left ventricle outflow valve of a complete heart. Valve 600 has fingers 630 similar to the valve shown in FIGS. 3 and 4. Balloon 640 is shown as exiting from a guide catheter 660, as is known in the art. One way to guide balloon 640 is by markers 650 which are implemented on balloon 640, as is known in the art. Markers 650 allow the balloon to be positioned using x-rays or fluoroscopically. Once a desired position for balloon 640 is achieved, balloon 640 is expanded, and valve 600 is secured to the tissue annulus. In one embodiment, the old valve may not require removal, but may just be compressed out of the way by expanding the new valve.

Figure 7:
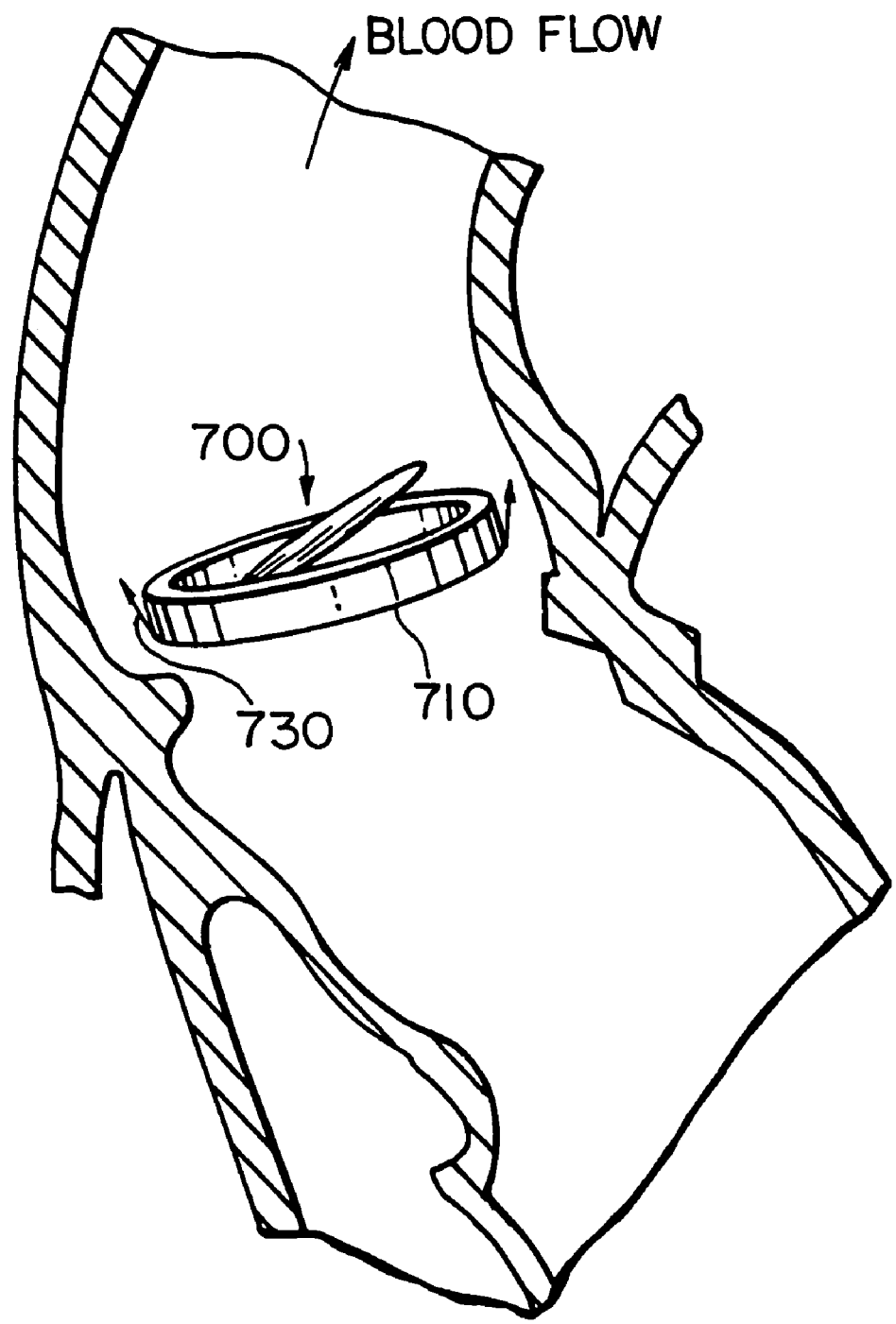
FIG. 7 is an elevational view of another embodiment of a heart valve according to the invention.

FIG. 7 shows an embodiment of a non-expanding valve 700 according to the principles of the invention. Valve 700 preferably includes fingers 730 that are oriented in a direction that is substantially parallel to the length of band 710 and are oriented in the direction of the blood flow. The exact orientation of the fingers can be configured before insertion. In this embodiment, once valve 700 is positioned within the tissue annulus, the surrounding tissue can be pulled up and over each retention finger. The tissue can be manipulated using a tweezers or other suitable tool.

The fingers described throughout this application are preferably formed from an elastic material—e.g., nitinol. The elasticity of the material allows the fingers to be expanded without undesirable deformation. The fingers may be heat-set to be flat against the length of band, 710, or to be slightly projecting out from band 710. During deployment through expansion of fingers 730, each flat individual finger 730 may be temporarily erected simultaneous to the tissue from the tissue annulus being pulled up and over the erected fingers. Thereafter, fingers 730 are released. When released, fingers 730 snap back to their original position, compressing and securing the tissue annulus to valve 700.

In an alternative embodiment of valve 700, retention fingers 730 may preferably be formed from relatively non-elastic, preferably annealed, stainless steel. Each finger is erected before deployment. Then, once the tissue annulus is pulled up and over each finger 730 such that the tissue annulus is pierced by each finger 730, the finger is crimped down against the valve body to secure the tissue annulus to valve 700.

Figure 8:
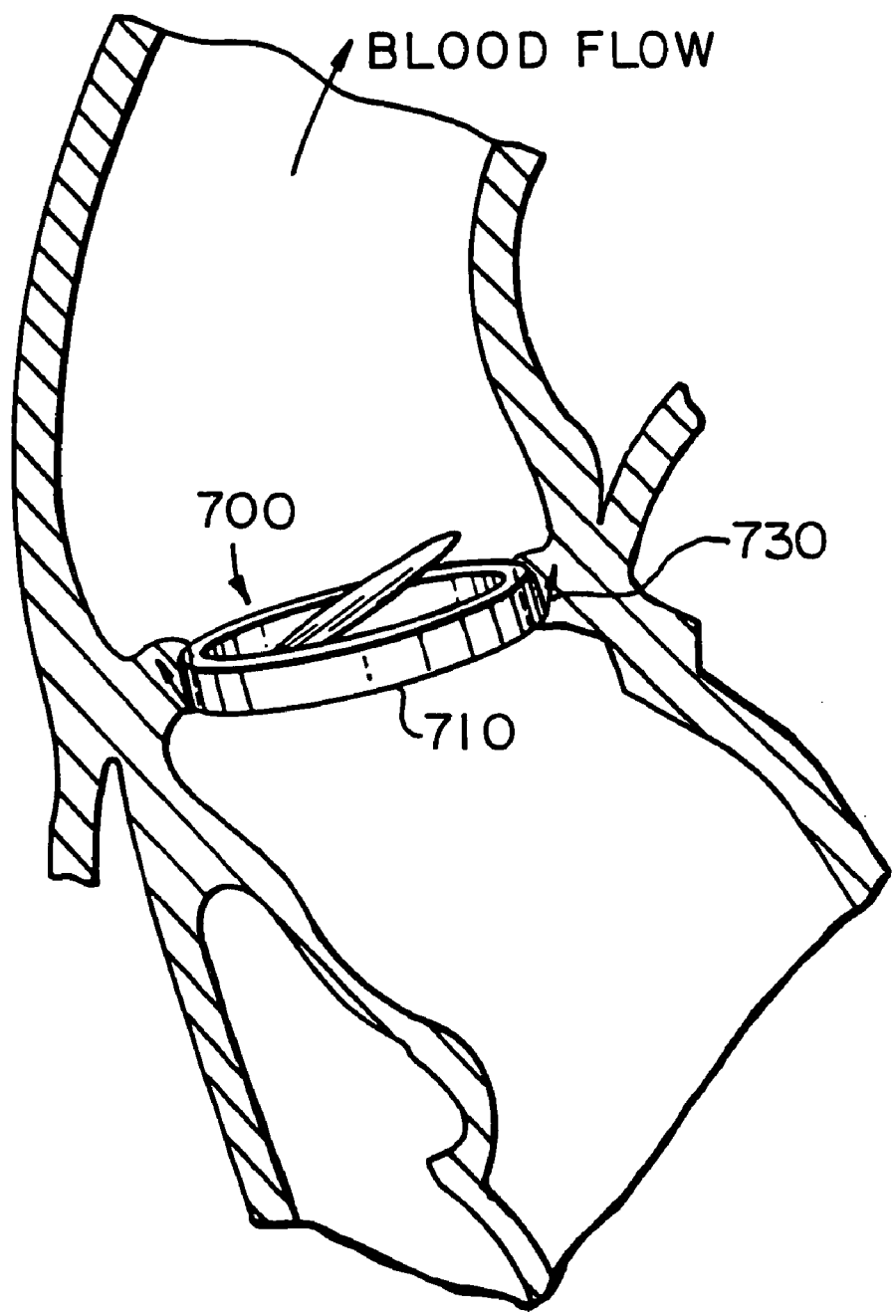
FIG. 8 is an elevational view of the heart valve of FIG. 7 in a deployed position.

FIG. 8 shows valve 700 after it has been deployed within the tissue annulus. In FIG. 8, fingers 730 secure valve 700 to the tissue annulus.

Figure 9:
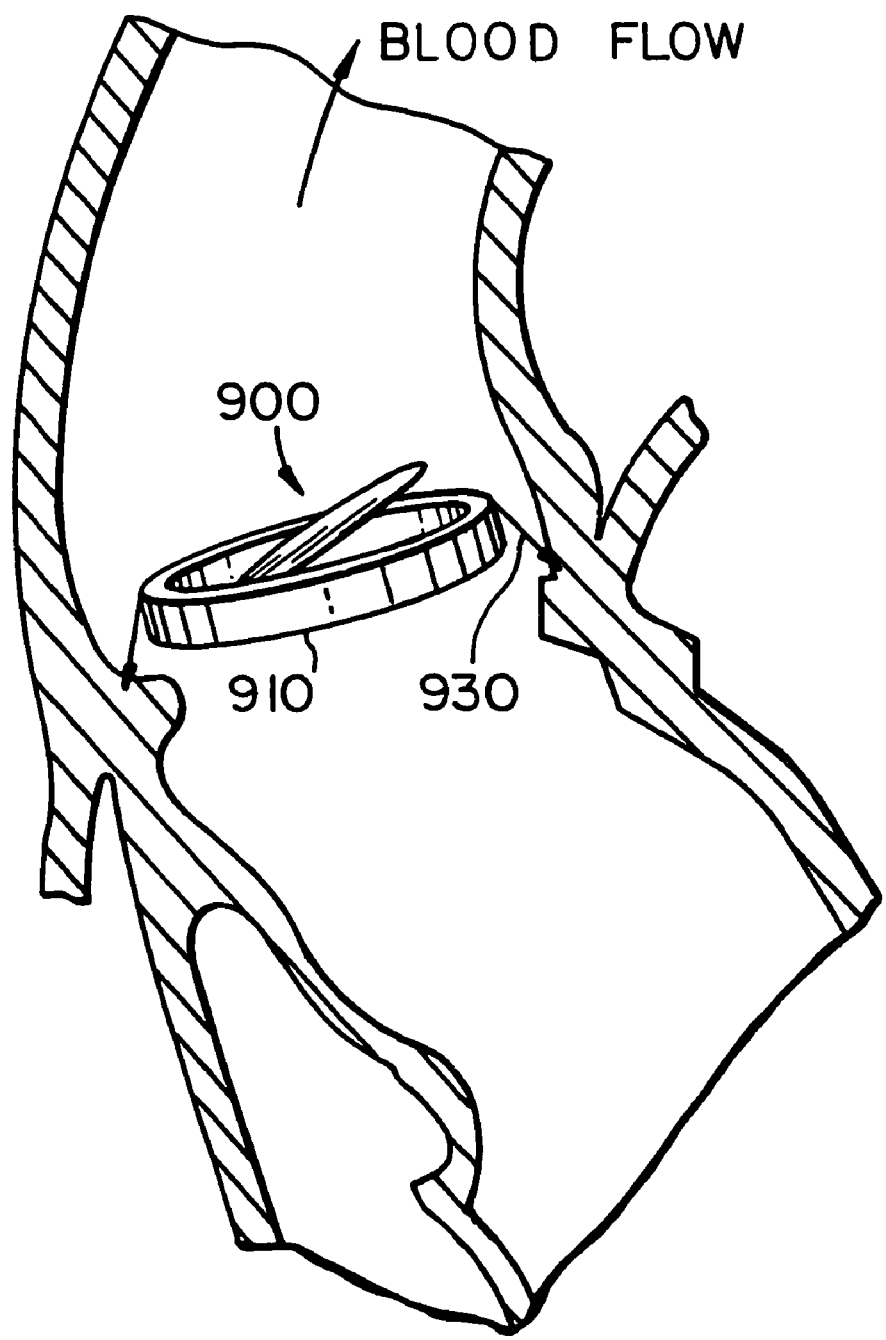
FIG. 9 is an elevational view of another embodiment of a heart valve according to the invention.
Figure 10:
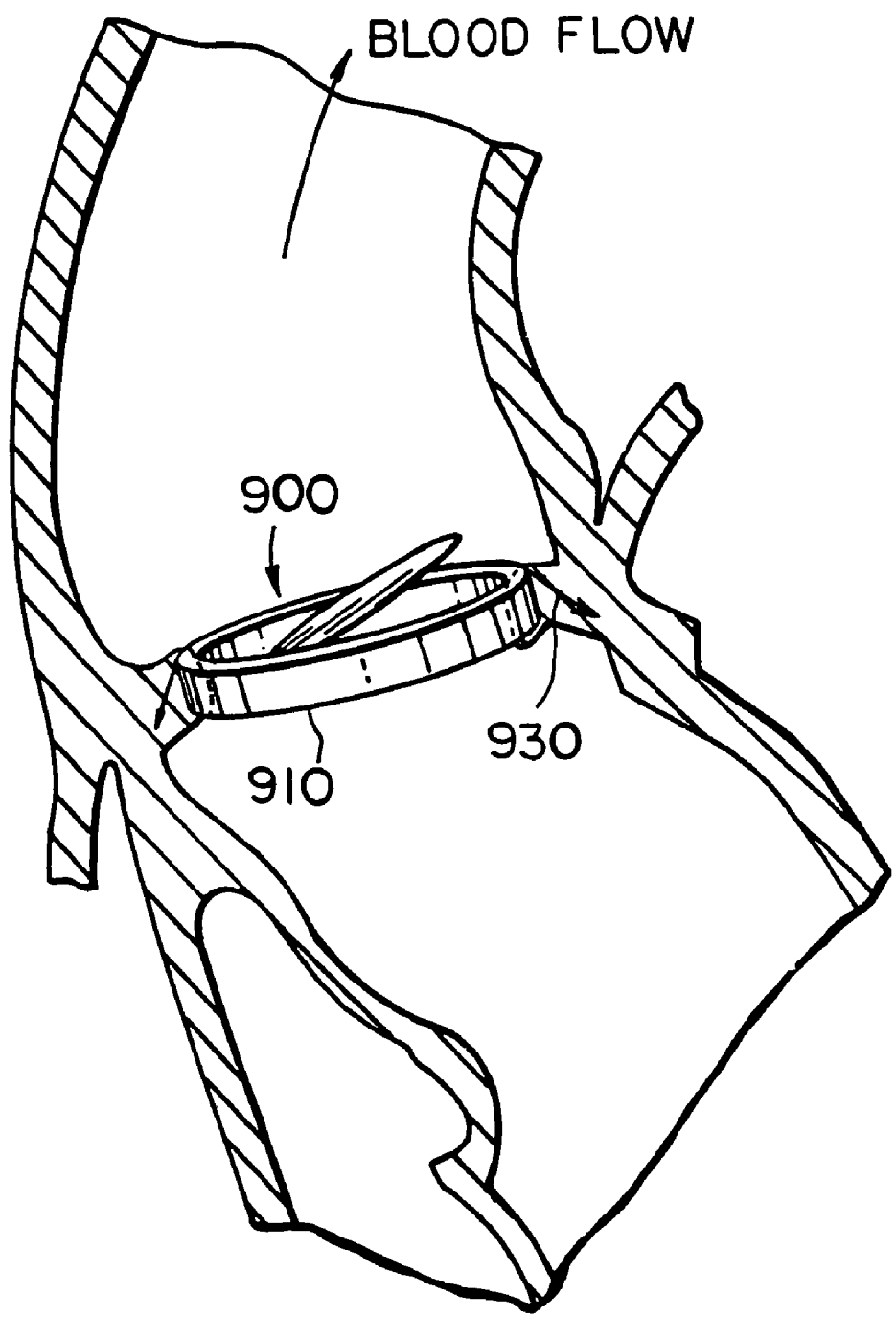
FIG. 10 is an elevational view of the heart valve of FIG. 9 in a deployed position.

FIGS. 9 and 10 show a valve 900 with fingers 930 oriented in a direction that is parallel to the length of band 710 but, unlike valve 700, is substantially opposite to the blood flow. One advantage of this embodiment is that fingers 930 are oriented in the direction of insertion which, in the case of the left ventricle outflow valve, is opposite the blood flow. Thus, the orientation of fingers 930 allows the surgeon to more readily advance the valve into the tissue annulus and to engage and secure the valve to the annulus. Another advantage of valve 900 is that the deployment of valve 900 does not require a tool to pull the flesh of the tissue annulus over the finger heads. Rather, valve 900 can be directly engaged to the tissue annulus by applying pressure to valve 900 opposite the direction of the blood flow.

Figure 11:
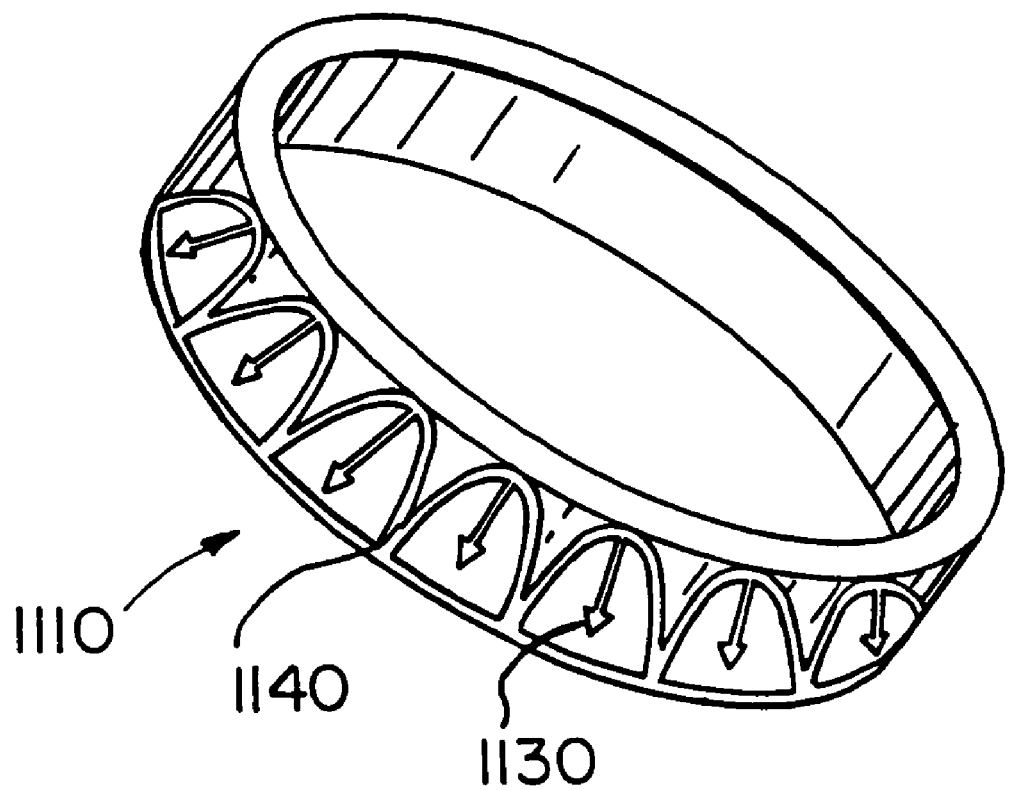
FIG. 11 is an elevational view of another connector band according to the invention.

FIG. 11 shows an embodiment of a preferably a non-expandable connector band 1110 for use in the valves shown in FIGS. 7–10. When band 1110 is inserted into the tissue annulus. Fingers 1130 and arches 1140 are caused to project outwards from band 1110. Fingers 1130 may be caused to project outwards when they are formed in the production process. When the band is expandable, it may be positioned within the tissue annulus, and, thereafter, the fingers are secured to the tissue annulus upon expansion of the band.

Figure 12:
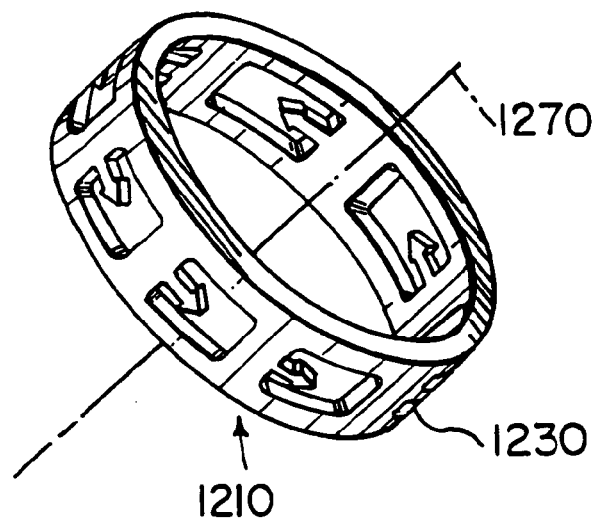
FIG. 12 is an elevational view of another connector band according to the invention.

FIG. 12 shows yet another embodiment of a valve 1210 according to the present invention. In valve 1210, fingers 1230 are oriented in a circumferential direction around the circumference of valve 1210.

Valve 1210 operates as follows: first, valve 1210 is positioned in the tissue annulus. This can be done by rotating valve 1210 into position (in the exemplary valve shown in FIG. 12, this requires a clockwise rotation around central longitudinal axis 1270) so fingers 1230 do not engage the tissue annulus. Then, valve 1210 is rotated in a counter-clockwise direction around central longitudinal axis 1270. This rotation causes fingers 1230 to pierce the tissue annulus. Thereafter, fingers 1230 return to their original position (or, in the case of stainless steel fingers, the fingers are mechanically crimped to return to their original position) and the valve 1210 is secured to the tissue annulus. Rotation of valve 1210 can be accomplished using a tool which may be designed to rotate valve 1210 or with another suitable technique.

Figure 13:
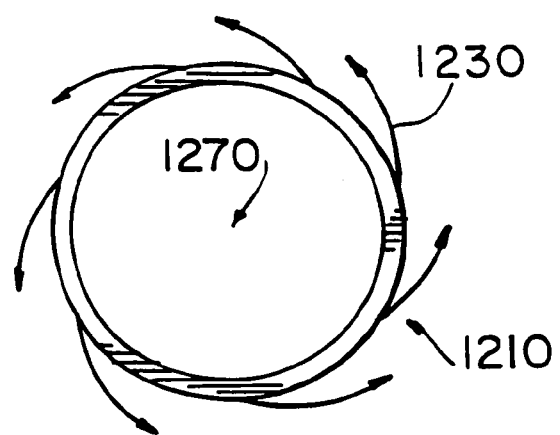
FIG. 13 is a top view of the connector band in FIG. 12.

FIG. 13 shows an end view of valve 1210. In this view, fingers 1230 are shown in a substantially fully expanded state.

Figure 14:
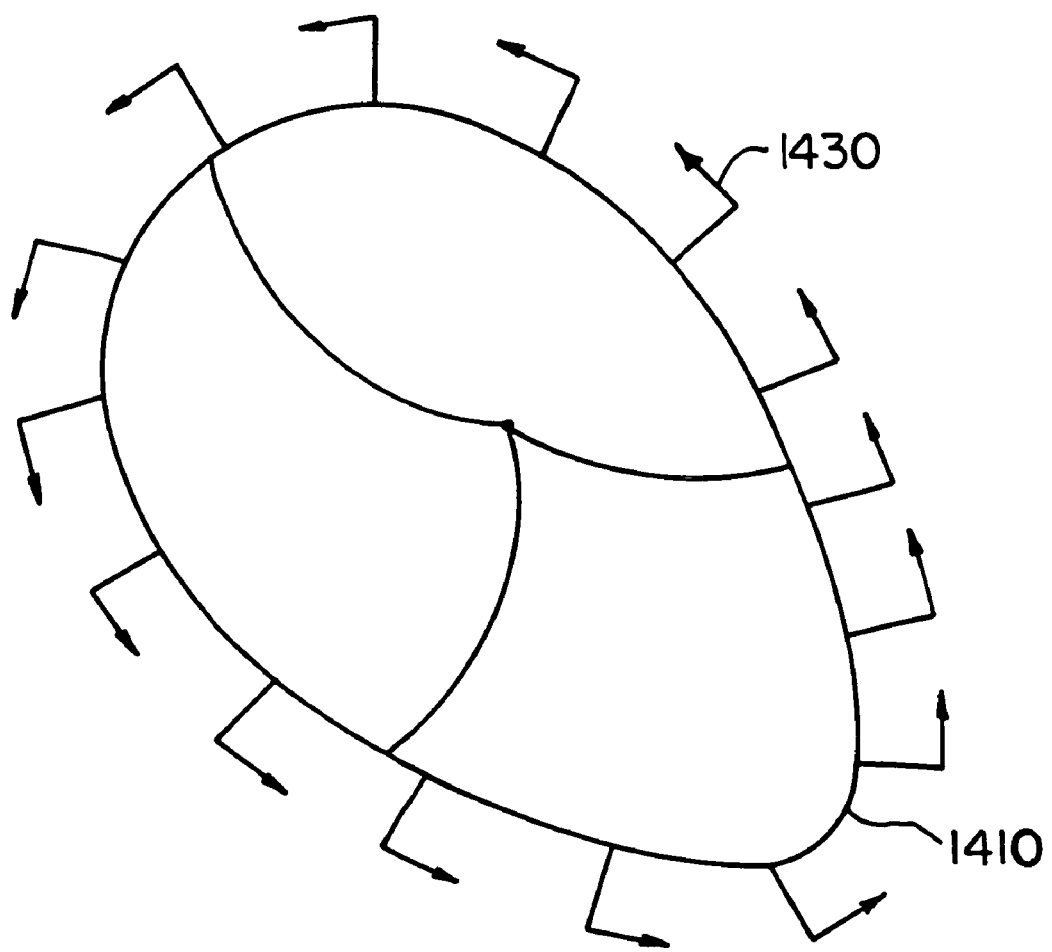
FIG. 14 is an elevational view of another embodiment of a heart valve according to the invention.

FIG. 14 shows another alternative embodiment of the invention wherein the fingers 1430 are preferably placed on the heart valve 1410 directly, without the interface of the connector band. In this embodiment, the fingers are distributed circumferentially around the heart valve, and the heart valve is inserted directly into the tissue annulus. Fingers 1430 may preferably be attached to heart valve 1410 in any of the possible configurations described herein.

In addition, though fingers 1430 are shown as hooked and barbed, they may be either hooked or barbed. As mentioned above, this feature of hooked and/or barbed fingers may preferably be used in each embodiment of the invention.

Each of the artificial heart valve attachment apparatus described herein preferably allows a replacement valve according to the invention to be implanted surgically or percutaneously.

The diameter of an exemplary expandable valve and/or connector band, like the valves and bands described herein in accordance with the present invention, is preferably between 3 and 5 millimeters before expansion. After expansion, the diameter of the valve and/or band is preferably between 15 and 20 millimeters. The length of the valve and/or band is preferably between 0.75 and 2 inches before expansion, and, after expansion, is preferably between 0.5 and 1.5 inches.

Materials that are suitable for use in a connector band according to the invention and as described herein, preferably include stainless steel or tantalum. These materials are relatively easily yieldable under balloon pressure when constructed as described above with either a bio-compatible mesh or with perforations, and are substantially radiopaque. The preferably substantially uni-directional valve element itself is flexible, preferably porcine, tissue (the valve element may allow for a minimal backflow of fluid upon the change in direction of fluid flow). The valve in the embodiment described above in which the connector band is deployed separate from the valve, is preferably a rigid valve formed from a suitable bio-compatible material—e.g., stainless steel—which may provide improved connectability with the connector band.

In addition, for the embodiments of the invention described herein, the number of fingers required may preferably be between 10 and 40 barbed or hooked fingers around the circumference of the valve, and most preferably 24 fingers. As mentioned above, the fingers may be formed from a variety of substances, including, but not limited to, nitinol or stainless steel.

Thus, an artificial heart valve attachment apparatus and methods that significantly reduce attachment times is provided. Persons skilled in the art will appreciate that the present invention can be practiced by other than the described embodiments, which are presented for purposes of illustration rather than of limitation, and the present invention is limited only by the claims which follow.

What is claimed is:

1. A valve apparatus for deploying in, and securing to, a tissue annulus, said valve comprising:
   a uni-directional valve portion for passing fluid in one direction and obstructing fluid in an opposite direction;
   a connector band located circumferentially around, and attached to, said valve portion; and a plurality of barbed fingers located circumferentially around, and attached to, said band, said fingers being oriented substantially parallel to the direction of blood flow and adapted to secure said valve to said tissue annulus.

2. The valve of claim 1, wherein said fingers can be expanded from a first position adjacent to said band, engaged to said tissue annulus, and returned to said first position following said engagement, thereby securing said band to said tissue annulus.

3. The valve of claim 1, wherein said fingers are formed from an elastic material.

4. The valve of claim 1, wherein said band comprises a gasket located around an outer circumference of said band, said gasket for sealing between said band and said tissue annulus.

5. The valve of claim 1, wherein said fingers are substantially parallel to a central longitudinal axis of said band.

6. A valve apparatus for deploying in, and securing to, a tissue annulus, said valve comprising:
  a uni-directional valve portion for passing fluid in one direction and obstructing fluid in an opposite direction, said valve having a fixed outer circumference; and
  a plurality of barbed fingers located circumferentially around, and attached to, the outer circumference of said valve, said fingers being oriented substantially parallel to the direction of blood flow and adapted to secure said valve to said tissue annulus.

7. The valve of claim 6, wherein said fingers are adapted to secure said valve to said tissue annulus upon deployment of said valve.

8. The valve of claim 6, wherein said fingers can be expanded from a first position adjacent to said valve, engaged to said tissue annulus, and returned to said first position following said engagement, thereby securing said valve to said tissue annulus.

9. The valve of claim 6, wherein said fingers are formed from an elastic material.

10. The valve of claim 6, wherein said valve comprises a gasket located around an outer circumference of said valve, said gasket for sealing between said valve and said tissue annulus.

11. The valve of claim 6, wherein said fingers are substantially parallel to a central longitudinal axis of said valve.

\* \* \* \* \*